(12) United States Patent
O'Leary et al.

(10) Patent No.: US 7,708,982 B2
(45) Date of Patent: May 4, 2010

(54) GELS FOR DISPENSING ACTIVE VOLATILE MATERIALS

(75) Inventors: Nicholas O'Leary, Slough (GB); Lyse Tranzeat, Melun (FR)

(73) Assignee: Firmenich SA, Geneva (CH)

( * ) Notice: Subject to any disclaimer, the term of this patent is extended or adjusted under 35 U.S.C. 154(b) by 1688 days.

(21) Appl. No.: 10/881,159

(22) Filed: Jun. 29, 2004

(65) Prior Publication Data

US 2004/0253285 A1 Dec. 16, 2004

Related U.S. Application Data

(63) Continuation of application No. PCT/IB03/002335, filed on Jun. 12, 2003.

(51) Int. Cl.
*A61L 9/04* (2006.01)
*A01N 25/26* (2006.01)
*A61K 7/46* (2006.01)

(52) U.S. Cl. .................. 424/76.1; 424/76.3; 424/76.4; 523/102; 512/4

(58) Field of Classification Search ............... 424/76.1, 424/76.3, 76.4; 523/102; 512/4
See application file for complete search history.

(56) References Cited

U.S. PATENT DOCUMENTS

| | | | | |
|---|---|---|---|---|
| 4,331,786 A | | 5/1982 | Foy et al. ..................... 525/408 |
| 4,734,278 A | | 3/1988 | Pougalan et al. ............ 424/76.3 |
| 4,864,014 A | | 9/1989 | Cuzin et al. .................. 528/279 |
| 5,539,034 A | | 7/1996 | Caupin et al. ................ 524/315 |
| 5,674,948 A | * | 10/1997 | Vonk ........................ 525/329.4 |
| 5,780,527 A | * | 7/1998 | O'Leary ..................... 523/102 |
| 6,528,556 B1 | * | 3/2003 | Herbst et al. ................. 523/122 |

FOREIGN PATENT DOCUMENTS

| | | |
|---|---|---|
| EP | 0 281 461 B1 | 4/1993 |
| EP | 0 671 123 B1 | 6/2000 |
| FR | 2 743 566 | 7/1997 |
| GB | 2 063 279 A | 6/1981 |
| WO | WO 97/26020 | 7/1997 |
| WO | WO 00/24434 | 5/2000 |

OTHER PUBLICATIONS

The Merck Index (11th Ed. 1989), p. 820.*

* cited by examiner

*Primary Examiner*—Mina Haghighatian
(74) *Attorney, Agent, or Firm*—Winston & Strawn LLP

(57) ABSTRACT

The present invention relates to the field of perfumery and more precisely it concerns a gel composition, and the consumer articles associated therewith, for dispensing an active volatile component in the surrounding space. The gel composition comprises a volatile liquid component and a thermoplastic polyether-ester-amide elastomer (PEEA).

8 Claims, No Drawings

GELS FOR DISPENSING ACTIVE VOLATILE MATERIALS

CROSS-REFERENCE TO RELATED APPLICATIONS

This application is a continuation of International application PCT/IB2003/002335 filed Jun. 12, 2003, the entire content of which is expressly incorporated herein by reference thereto.

TECHNICAL FIELD

The present invention relates to the field of perfumery and more precisely it concerns a gel composition, as well as the consumer articles associated therewith, for dispensing an active volatile component in the surrounding space. The gel composition comprises an active volatile liquid component and a thermoplastic polyether-ester-amide elastomer (PEEA).

PRIOR ART

Active volatile material dispensers, such as air-fresheners, are consumer products commonly used in every day life, and several different types thereof are known. However, most of these devices contain a limited amount of active volatile component and therefore the total mass of carrier required to deliver a suitable level of active volatile component, e.g. a perfume, is relatively high. Examples of known products include hydrogel devices, or wick-type devices, which contain, in general, only up to 15% of active volatile component, relative to the total weight of the device.

Therefore, there is a need to develop devices capable of carrying high amounts of active volatile and delivering the latter over a prolonged period while using small amounts of carrier such as resins, support of said resins and/or packaging.

A few solutions to the above-mentioned problem have been proposed, but none have been completely satisfactory.

In WO 00/24434 there is disclosed a solid gel composition containing up to 90% of perfume, a functionalized polymer such as a maleinized polybutadiene or polyisoprene, and a cross-linking agent of complementary functionality such as a polyoxyalkylenediamine.

That composition suffers from the drawback of imposing some limitations on the perfume formulation, as some perfuming ingredients such as esters, aldehydes and alcohols may react with the functionalized polymer and/or cross-linking agent and thus alter the fragrance of the perfume and the polymer's releasing properties. Moreover, the preparation and use of such a gel are such that it is preferable to associate the latter with a support, and therefore the amount of perfume, relative to the amount of carrier, is still limited.

In WO 97/26020 there is mentioned the possibility of having a composition containing up to 95% of perfume, together with a polymer of the polyether-ester-amide type. However the methods of preparation of the composition which are described in said patent, i.e. the "drageoir" or the "master batch" methods, do not make it possible to obtain a uniform composition containing more than 55% of perfume, in spite of the inventors' claims. In fact we have ascertained that when the "drageoir" method, as disclosed in said patent application, and high quantities of perfume (e.g. more than 60%) are used, the polyether-ester-amide polymer is not able to entrap the totality of the perfume and thus the resulting products are mixtures of swollen resins soaking in the excess of perfume. The other manufacturing process disclosed in said application, namely the "master batch" method, which consists in the extrusion of the granules obtained by the "drageoir" method, allows even lower perfume loads. In other words, despite the claim that the known composition has up to 95% of perfume, the content of WO 97/26020 does not in fact allow a person skilled in the art to produce compositions containing more than 55% of perfume. Moreover, the compositions obtained according to WO 97/26020, unless containing small amounts of perfume, are not self-supporting and therefore require the use of particular packaging, limiting thus the possibility to reduce the amount of carrier.

Therefore, in order to limit the total mass of the volatile material dispenser, while maintaining high performance of fragrance delivering and a prolonged fragrance diffusion into the surrounding environment, there is still a need for a composition which is solid, self-supporting, capable of fully entrapping high quantities of active volatile and imposing a minimal constraint on the choice of the volatile composition to be used.

SUMMARY OF THE INVENTION

The present invention relates to a new gel composition, of simple preparation and which is self-supporting at room temperature, e.g. a rubber-like solid. This gel composition is capable of incorporating high amounts of an active volatile, i.e. up to 97.5% of the total composition, and of being able to dispense the latter into the surroundings. By "active volatile" it is meant here an ingredient, substance or composition capable of bringing a benefit or effect into its surrounding environment, and in particular a perfuming, insect repellent or attractant, insecticide, antibacterial or fungicide effect.

Consequently, the gel composition of the present invention comprises:

a) between 97.5% and 70%, based on the weight of the gel composition, of an active volatile liquid component, and b) between 2.5% and 30%, based on the weight of the gel composition, of a thermoplastic polyether-ester-amide elastomer (PEEA) of formula

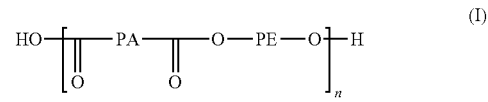

(I)

wherein PA represents the polyamide moiety and PE represents the polyether moiety and the index n stands for an integer designating the multiple of the recurrent pattern.

The resulting gel composition has a storage modulus higher that is than its loss modulus, so that the gel composition behaves as a rubber-like solid.

The invention also relates to gel compositions made according to a preferred manufacturing process as well as to the use of such gel compositions in various consumer articles or products. The manufacturing process itself represents yet another embodiment.

DETAILED DESCRIPTION OF THE PREFERRED EMBODIMENTS

The storage modulus is the ability of the material to store energy and is related to the stiffness of the material. The loss modulus represents the energy dissipated by the material and reflects the damping characteristics of the material.

The gel according to the invention can also comprise, as optional components, at least one of the ingredients selected from the group consisting of antioxidants, UV-inhibitors, oil soluble dyes, solvents and bittering agents.

The active volatile liquid component of the invention's gel is intended to be dispersed into the surrounding air or enclosed space, such as rooms, cupboards, drawers, etc, by the composition of the invention. Said active volatile liquid component is composed essentially of one or more active volatile materials and may possibly contain one or more suitable solvents, e.g. a solvent of current use in functional perfumery.

In order to facilitate the formation of the invention's gel, the active volatile liquid component will preferentially contains a limited total amount of hydroxy derivatives, i.e. compounds having at least an hydroxy group, examples of which are alcohols or glycols.

The maximum amount of hydroxy derivatives which can be present in the active volatile liquid component will depend on the exact nature of said derivatives, on the number of said derivatives and also on total amount of the active volatile liquid component used in the invention's gel. A person skilled in the art will be able to define such maximum amount by using its general knowledge and a limited number of routine experiments. However, as non-limiting example, one may cite active volatile liquid component which, when used at a level of 90% relative to the total weight of the invention gel, may contain up to 80% of tertiary alcohols or up to 40% of primary alcohols.

As the active volatile materials there can be used, for example, perfumes or perfuming ingredients, in which case the consumer product will be of the air freshener type. Other suitable active volatile materials can be a deodorizing or sanitizing agent or any other volatile material capable of imparting perceptible and desirable benefits to the quality of the air into which it is diffused.

As perfume or perfuming ingredients there can be used any ingredient or mixture of ingredients currently used in perfumery. The latter can be made of discreet chemicals. More often, however, it will be a more or less complex mixture of volatile ingredients of natural or synthetic origin. The nature of these ingredients can be found in specialized books of perfumery, e.g. in S. Arctander (Perfume and Flavor Chemicals, Montclair N.J., USA 1969) or similar textbooks of reference, and a more detailed description thereof is not warranted here.

Although special mention has been made hereinabove of the perfuming effect that can be exerted by the compositions of the invention, the same principles apply to the manufacture of analogous compositions for the diffusion of deodorizing or sanitizing vapors, the perfume being replaced by a deodorizing composition, a antibacterial, an insecticide, an insect repellent or an insect attractant. By the term "sanitizing vapors", we refer here not only to the vapors of those substances which can enhance the degree of acceptance of the air surrounding the observer, but also to those substances which can exert an attractant or repellent effect toward certain species of insects, for instance toward houseflies or mosquitoes, or else, which can have bactericide or bacteriostatic activity. It goes without saying that mixtures of such agents can also be used.

As mentioned above, the active volatile liquid component may possibly also comprise a suitable solvent. The presence of a solvent may be useful to have a monophasic liquid or to modulate the speed of evaporation of the volatile into the surrounding air. Said solvents may belong to the families of isoparaffins, paraffins, hydrocarbons, glycol ethers, glycol ether esters, esters or ketones.

Examples of commercially available solvents useful to the invention are known under the tradename ISOPAR® H, J, K, L, M, P or V (isoparaffins; origin: Exxon Chemical), NORPAR® 12 or 15 (paraffins; origin: Exxon Chemical), EXXSOL® D 155/170, D 40, D 180/200, D 60, D 70, D 80, D 100, D 110 or D 120 (dearomatized Hydrocarbons; origin: Exxon Chemical), DOWANOL® PM, DPM, TPM, PnB, DPnB, TPnB, PnP or DPnP (glycol ethers; origin: Dow Chemical Company), EASTMAN® EP, EB, EEH, DM, DE, DP or DB (glycol ethers; origin: Eastman Chemical Company) DOWANOL® PMA or PGDA (glycol ether esters; origin: Dow Chemical Company) or EASTMAN® EB acetate, EASTMAN® DE acetate, EASTMAN® DB acetate, EASTMAN® EEP (all glycol ether esters; all origin: Eastman Chemical Company). Other examples of solvents useful to the invention are dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

The amount of solvent present in the active volatile liquid component may vary over an extended range and one can cite, as non-limiting example, amounts comprised between 0% to 40%, preferably between 0% to 30%, the percentage being relative to the weight of the active volatile liquid component.

A person skilled in the art of preparing a volatile liquid component will be perfectly able to choose the ingredients, as well as their concentrations, needed for the manufacture of an active volatile liquid component imparting the desired benefits and, at the same time, allowing the formation of the invention's gel.

The compositions of the invention may contain the volatile liquid component in an amount comprised between 70% and 97.5%, the percentages being relative to the total weight of the composition. In a preferred embodiment of the invention, the volatile liquid component is present in an amount comprised between 80% and 96%, and even more preferably in an amount comprised between 87% and 95%.

The second component of the invention gel composition is an elastomer. This polymer is in fact the constituent that provides the mechanical behavior of the invention's gel composition.

This elastomer is a thermoplastic polyether-ester-amide elastomer (PEEA polymer) of formula

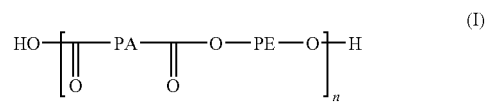

(I)

wherein PA represents the polyamide moiety and PE represents a linear or branched polyoxyalkylene glycol moiety, in which the alkylene radical has at least 2 carbon atoms, and the index n stands for an integer designating the multiple of the recurrent pattern.

The PEEA polymers may be the result of the copolymerization, in the melting phase, of a dicarboxylic polyamide moiety having a terminal carboxylic function of mean molecular weight comprised between 300 and 15000, and a linear or branched aliphatic polyoxyalkylene glycol having terminal hydroxylic functions and a mean molecular weight comprised between 200 and 6000. Said reaction is carried out under substantial reduced pressure and at a temperature comprised between 100° C. and 400° C. in the presence of a catalyst consisting of a tetraalkylorthotitanate of general formula $Ti(OR)_4$, wherein R represents a $C_1$-$C_{24}$ linear or branched aliphatic hydrocarbon radical and wherein its weight proportion with respect to the reaction mixture is comprised between 0.01% and 5%. Alternatively, the PEEA polymers may be the result of the co-polymerization, under conditions similar to that mentioned hereinabove, between a polyamide having terminal diamino function and a polyoxyalkylene glycol having terminal dicarboxylic function.

The thermoplastic polyether-ester-amide elastomers are best known under the commercial name of PEBAX® (origin: ATOFINA, France), and some of them are described in U.S. Pat. No. 4,331,786, U.S. Pat. No. 4,864,014, GB 2063279, EP 281461 or in related patents.

Any type of PEBAX® may be used for the purpose of the invention, provided that it is able to entrap at least more than 2.3 times its own weight of perfume, preferably more than 5 times its own weight.

Preferred elastomers are those having a melting point, measured according to the norm ASTM D 789, comprised between 170° C. and 100° C., and possibly also a hardness Shore A comprised between 60 A and 92 A, measured according to the norm ASTM D 1484. Examples of such PEBAX® are the grades 4033, 3533 or 2533.

In a more preferred embodiment of the invention, the elastomer has a hardness Shore A comprised between 70 A and 85 A or a hardness Shore D comprised between 35 D and 20 D, such as PEBAX® 3533 or 2533.

As previously described, the compositions of the invention are characterized by the fact that the polymer is present in an amount comprised between 2.5% and 30%, the percentages being relative to the total weight of the composition. In a preferred embodiment of the invention, the polymer is present in an amount comprised between 4% and 20%, relative to the weight of the gel composition.

As anticipated above, it is possible to add to the gel composition of the invention some optional components acting as, for example, antioxidant, UV-inhibitors, dye, solvents or even bittering agents.

As non-limiting examples of useful antioxidant components, one can cite the sterically hindered amines, i.e. the derivatives of the 2,2,6,6-tetramethyl-piperidine, such as those known under the tradename UVINUL® (origin BASF AG) or TINUVIN® (origin: Ciba Specialty Chemicals), as well as the alkylated hydroxyarene derivatives, such as butylated hydroxytoluene (BHT).

The antioxidant component may be incorporated in the composition according to the invention in an amount comprised between 0% and 3%, the percentages being relative to the total weight of the composition. Preferably, the antioxidant component is present in amounts comprised between 0.1% and 2%.

As non-limiting examples of useful UV-inhibitor components, one can cite benzophenones, diphenylacrylates or cinnamates such as those available under the trade name UVINUL® (origin: BASF AG).

The UV-inhibitor component may be incorporated in the composition according to the invention in an amount comprised between 0% and 0.5%, the percentages being relative to the total weight of the composition. Preferably, the UV-inhibitor component is present in amounts comprised between 0.01% and 0.4%.

Dyes are another optional components of the invention composition. Suitable dyes are oil-soluble. Non-limiting examples of suitable dyes are derivatives of the anthraquinone, methines, azo, triarylmethane, triphenylmethane, azine, aminoketone, spirooaxine, thioxanthane, phtalocyanine, perylene, benzopyran or perinone families. Example of such dyes which are commercially available are known under the tradename SANDOPLAST® Violet RSB, Violet FBL, Green GSB Blue 2B or SAVINYL® Blue RS (all anthraquinone derivatives, origin: Clariant Huningue S. A.), OILSOL® Blue DB (anthraquinone; origin: Morton International Ltd.), SANDOPLAST® Yellow 3G (methine, origin: Clariant Huningue S. A.), SAVINYL® Scarlet RLS (azo metal complex origin: Clariant Huningue S. A.), OILSOL® Yellow SEG (monoazo; origin: Morton International Ltd.), FAT ORANGE® R (monoazo; origin: Hoechst AG), FAT RED® SB (diazo; origin: Hoechst AG), NEOZAPON® Blue 807 (phtalocyanine; origin: BASF AG), FLUOROL® Green Golden (perylene; origin: BASF AG).

The dye component may be incorporated into the composition according to the invention in an amount comprised between 0% and 1%, the percentages being relative to the total weight of the composition. Preferably, the dye component is present in amounts comprised between 0.005% and 0.5%.

The presence of a bittering agent may be desirable in order to render the product unpalatable, making it less likely that the composition is ingested, especially by young children. One can cite, as non-limiting example, isopropyl alcohol, methyl ethyl ketone, methyl n-butyl ketone or yet a denatonium salt such as the denatonium benzoate known also under the trademark BITREX™ (origin: Mac Farlan Smith Ltd.).

The bittering component may be incorporated into the composition according to the invention in an amount comprised between 0% and 6%, the percentages being relative to the total weight of the composition. In the case of BITREX® the maximum amount can be lowered to up to 0.1% of the total weight of the composition.

Preferably, the bittering component is present in amounts comprised between 0.5% and 5%. In the case of BITREX® these amounts can be comprised between 0.001% to 0.05% of the total weight of the composition.

The gel compositions of the invention are obtainable by a manufacturing process comprising the following steps:

a) heating, in a vessel, a mixture of the active volatile liquid component, the elastomer, and if required the optional compounds, at a temperature comprised between 90° C. and 150° C., b) once the polymer is fully dissolved, allowing the solution to cool to a temperature comprised between 60° C. and 100° C., and c) pouring the solution obtained in b) into a mold or container, having an appropriate shape, to obtain the composition of the invention.

Preferably the process is performed in a closed or pressured vessel, in order to avoid loss of volatile components, alternatively the vessel is equipped with a condenser.

The heating step is an essential one, as we have discovered that by simply mixing the active volatile liquid component and the polymer at room temperature, or similar, it is not possible to obtain a sufficiently homogeneous mixture of the ingredients and consequently it is not possible to obtain a gel composition according to the invention, i.e. a rubber-like solid composition.

Another advantage of said manufacturing process resides in the fact that by pouring the homogeneous mixture of the volatile liquid and the resin into an appropriate mould or container, it is possible to obtain directly the composition in an appropriate shape without any additional strong heating steps such as an extrusion step.

As anticipated above, the gel composition of the invention is particularly suitable for the manufacture of a consumer article for dispensing a volatile material in the surrounding space. Thus, a consumer article containing, or associated with, a gel composition according to the invention is also an object of the present invention.

Such a consumer article can be, depending on the nature of the volatile liquid component used in the preparation of the gel composition, a perfuming or sanitizing device such as an air freshener, particularly of the solid or gel type, a diaper pail freshener, a car freshener, a closet freshener, a cat litter box freshener, a shoe freshener or a garbage pail freshener, an insecticide or an insect repellent device.

The consumer article of the invention, to the contrary of those of the prior art previously cited, can simply consist in the invention gel composition, molded in an appropriate shape, i.e. a support of the gel is not required. The gel composition of the invention may have any suitable shape.

It is also understood that the invention's gel may also be associated with a container housing said composition. In such a case, different types of containers can be used. As non limiting examples, one can cite a container made of a material totally impermeable to the vapors of the volatile liquid component and which possesses at least an aperture through which the vapors of the volatile liquid component can be diffused into the air surrounding said consumer article. Alternatively the container can envelope entirely the gel and at least a portion of said container is made of a material which allows the escape of the vapors of the volatile liquid component into the air surrounding said consumer article.

Whatever or not the consumer article includes a container, in order to prevent diffusion of vapors of the volatile liquid into the surroundings during storage, said consumer article, or the portion of the container which is permeable to the volatile liquid's vapors, can be sealed by any known means, such as a plastic film, which is impermeable to the volatile liquid phase vapors. The consumer will then activate the consumer article simply by removing the sealing, after which the volatile liquid phase will start to diffuse into the surrounding air.

EXAMPLES

The invention will now be described in further detail by way of the following examples.

Example 1

Preparation of Perfumed Gel Composition According to the Invention 61.38 g of perfume base (Tropical 438872, origin: Firmenich S. A.) were added to 6.82 g of polymer (PEBAX® 2533 SA 01 granules, origin: Atofina) in a 100 ml two-necked round bottom flask, fitted with a 200 mm Leibig condenser and thermometer. The flask was placed in an electronic stirrer/heating mantle, and the contents heated with continuous stirring to 120-135° C., whereupon the polymer granules dissolved in the perfume base. Stirring was continued for a further 5 minutes to ensure complete dissolution of the polymer. The resulting mixture was cooled to approximately 90° C., and five shallow glass containers (with surface area approximately 18 cm$^2$) each filled with 6.50 g. After cooling to room temperature the composition had formed a transparent, self-standing, rubber-like gel, which contained 90% by weight of the perfume base.

The initial weight of the samples was recorded, and they were then placed in a temperature/humidity controlled test room. The weight of each sample was recorded at regular intervals thereafter, up to 30 days after commencement of the test. 70% of the original weight of the perfume base evaporated from the gel in 30 days.

Example 2

Preparation of Perfumed Gel Composition According to the Invention

A fragrance base composition was prepared by admixing the following ingredients:

| Ingredient | Parts by weight |
| --- | --- |
| Dimethylbenzyl carbinyl acetate | 1.50 |
| cis-3-Hexenyl acetate | 0.30 |
| Undecanal | 0.03 |
| Diethyl phthalate | 4.94 |
| gamma-Nonalactone | 0.40 |
| Bergamot essential oil | 4.60 |
| Ethyl butyrate | 0.10 |
| Cassis Base 345 B[1)] | 3.80 |
| Tricyclodecenyl propionate | 2.30 |
| Coumarin | 0.20 |
| HABANOLIDE ®[2)] | 11.50 |
| Piperonal | 0.50 |
| Allyl heptanoate | 1.20 |
| ISO E SUPER ®[3)] | 10.70 |
| Mandarin oil expressed | 3.80 |
| Muscenone[4)] | 0.50 |
| 2-Methyl-4-(2',2',3'-trimethyl-3'-cyclopenten-1'-yl)-4-pentenal | 10.00 |
| Ethyl-2-methylbutyrate | 1.20 |
| 1-(5,5-Dimethyl-1-cyclohexen-1-yl)-4-penten-1-one | 0.20 |
| Methyl octine carbonate | 0.03 |
| Rose oxide | 0.20 |
| Orange oil | 20.00 |
| Veloutone[5)] | 1.20 |
| ortho-Butylcyclohexyl acetate | 29.00 |
| 2,4-Dimethylformyl-3-cyclohexene | 0.80 |
| | 100.00 |

[1)]compounded perfumery base; origin: Firmenich SA, Geneva, Switzerland
[2)]pentadecenolide; origin: Firmenich SA, Geneva, Switzerland
[3)]origin: IFF, USA
[4)]3-methyl-cyclopentadecenone; origin: Firmenich SA, Geneva, Switzerland
[5)]2,2,5-trimethyl-5-pentyl-cyclopentanone; origin: Firmenich SA, Geneva, Switzerland Switzerland 65.79 g of the perfume base were added to 7.31 g of PEBAX ® 2533 SA 01 granules (origin: Atofina) in a 100 ml two-necked round bottom flask, fitted with a 200 mm Leibig condenser and thermometer. The flask was placed in an electronic stirrer/heating mantle, and the contents heated with continuous stirring to 120-135° C., whereupon the PEBAX ® granules dissolved in the perfume base. Stirring was continued for a further 5 minutes to ensure complete dissolution of the PEBAX ®. The resulting mixture was cooled to approximately 90° C., and five shallow glass containers (with surface area approximately 18 cm$^2$) each filled with 6.50 g. After cooling to room temperature the composition had formed a transparent, rubber-like gel, which contained 90% by weight of the perfume base.

A perfume load of 90%, means that, to absorb the same quantity of perfume, the compositions according to the invention need four times less resin than the compositions disclosed in WO 97/26020, which contain up to 55% of perfume, representing thus a consistent reduction of support resin.

Example 3

Preparation and Mechanical Characterization of Perfumed Gel Compositions According to the Invention Perfume gels were prepared according to the method described in Example 1, using four perfume bases, namely:
Tropical 438872 (origin: Firmenich SA)
Spring Blossom 150531 BG (origin: Firmenich SA)
Citrowood 150783 (origin: Firmenich SA)
Cantina 150685 F (origin: Firmenich SA)

Dynamic Mechanical Analysis was used to characterize the mechanical properties of the perfume gels. Compression mode measurements were performed using a parallel-plate type dynamic mechanical analyser (DMA 2980, origin: TA Instruments), equipped with a thermocontroller. The storage modulus (M'), loss modulus (M") and tan δ were measured under the conditions shown in Table 1:

TABLE 1

Conditions of the mechanical measurements

| Instrument | TA Instruments DMA 2980 |
|---|---|
| Mode | Multi-frequency compression |
| Tools | Clamp compression |
| Sample geometry | Cylindrical (thickness = 2.5 mm to 3.5 mm, diameter = 9.06 mm) |
| Test temperature | 25° C. |
| Static tension | 1 N |
| Frequency | 1 Hz |
| Amplitude | 20 μm |

The storage modulus (M') is the ability of the material to store energy and is related to the stiffness of said material. The loss modulus (M") represents the energy dissipated by the material and reflects the damping characteristics of the material.

The values of M' and M" for the samples are given in Table 2, the range quoted is that for the three replicates tested for each sample.

TABLE 2

Range values of the storage modulus (M') and the loss modulus (M")

| Fragrance Base | Fragrance Dosage | M' (MPa) | M" (MPa) |
|---|---|---|---|
| Tropical 438872 | 90% w/w | 0.030 to 0.036 | 0.026 to 0.028 |
| Spring Blossom 150531 BG | 90% w/w | 0.082 to 0.097 | 0.039 to 0.044 |
| Citrowood 150783 | 90% w/w | 0.072 to 0.102 | 0.020 to 0.025 |
| Cantina 150685 F | 90% w/w | 0.044 to 0.049 | 0.023 to 0.026 | w/w = percentage relative to the weight of the composition

Under the conditions tested, the storage modulus for the gel is higher than the loss modulus. As a result the deformations are reversible and the gels behave as rubber like samples. Moreover, the gels were self-supporting.

Example 4

Preparation of Perfumed Gel Composition According to the Invention Having Different Perfume Concentration A perfumed gel was prepared using the equipment and the method described in Example 1. As active volatile liquid component was used a perfume, namely Spring Blossom 150531 BG (origin: Firmenich SA). Additional perfume gels, with lower levels of PEBAX® 2533 SA 01 as detailed in Table 3, were prepared using the same perfume.

TABLE 3

Composition of various perfumed gel according to the invention

| Mass of perfume | Mass of PEBAX® 2533 SA 01 | PEBAX® concentration in the resulting gel | Observations |
|---|---|---|---|
| 58.73 g | 5.11 g | 8% | Rubber-like, transparent, hard gel produced. |
| 60.85 g | 3.88 g | 6% | Rubber-like, transparent, hard gel produced. |
| 59.61 g | 2.48 g | 4% | Rubber-like, transparent, soft gel produced. |
| 61.11 g | 1.57 g | 2.5% | Rubber-like, transparent, soft gel produced. | percentages being relative to the total weight of the composition

As Table 3 indicates, it is possible to obtain gel according to the invention with an amount of resin as low as 2.5% of the total weight of the composition. This means that, by using a manufacturing method according to the invention, the PEBAX® resin is able to entrap up to 40 times its own weight of perfume.

What is claimed is:

1. A process for manufacturing a gel composition consisting essentially of the following steps:
    admixing the following ingredients:
    i) between 97.5% and 70% of a first mixture of volatile liquid perfuming ingredients;
    ii) between 2.5% and 30% of a thermoplastic polyether-ester-amide elastomer of formula

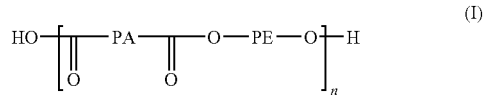

(I)

wherein PA represents the polyamide moiety and PE represents the polyether moiety and the index n stands for an integer designating the multiple of the recurrent pattern;
    iii) optionally an antioxidant, an UV-inhibitor, an oil soluble dye, a solvent and/or a bittering agent, with the percentages being defined by weight, relative to the total weight of the gel composition,
    to form a second mixture composition consisting essentially of the recited ingredients;
    heating, in a vessel, the second mixture at a temperature of between 90° C. and 150° C., with the vessel being closed, pressured or equipped with a condenser, to form a solution where the polymer is combined with the mixture of the volatile perfuming ingredients and the additional ingredients;
    once the polymer is fully dissolved, allowing the solution to cool to a temperature of between 60° C. and 100° C.; and
    pouring the solution into a mold or container having an appropriate shape to obtain the gel composition of the invention.

2. A process according to claim 1, wherein the mixture of volatile liquid perfuming ingredients is present in an amount of between 80% and 96%, the percentages being relative to the total weight of the composition.

3. A process according to claim 1, wherein the elastomer has a melting point of between 170° C. and 100° C. and a Shore A hardness of between 60 A and 92 A.

4. A process according to claim 1, wherein the elastomer has a Shore A hardness of between 70 A and 85 A.

5. A process according to claim 1, wherein the elastomer is present in an amount of between 4 and 20%, relative to the weight of the gel composition.

6. A process according to claim 1, wherein the antioxidant compound is a sterically hindered amines or an alkylated hydroxyarene derivatives.

7. A process according to claim 1, wherein the dye is a derivative of the anthraquinone, methines, azo, triarylmethane, triphenylmethane, azine, aminoketone, spirooaxine, thioxanthane, phtalocyanine, perylene, benzopyran or perinone families.

8. A process according to claim 1, wherein the bittering agent is isopropyl alcohol, methyl ethyl ketone, methyl n-butyl ketone or a denatonium salt.

* * * * *